(12) United States Patent
Kambara et al.

(10) Patent No.: US 8,975,066 B2
(45) Date of Patent: Mar. 10, 2015

(54) DNA ANALYSIS APPARATUS

(75) Inventors: Hideki Kambara, Hachioji (JP);
Akihiko Kishimoto, Kokubunji (JP)

(73) Assignee: Hitachi, Ltd., Tokyo (JP)

( * ) Notice: Subject to any disclaimer, the term of this patent is extended or adjusted under 35 U.S.C. 154(b) by 956 days.

(21) Appl. No.: 12/419,399

(22) Filed: Apr. 7, 2009

(65) Prior Publication Data
US 2009/0253194 A1 Oct. 8, 2009

(30) Foreign Application Priority Data

Apr. 8, 2008 (JP) ................................. 2008-100592

(51) Int. Cl.
| | |
|---|---|
| *C12M 1/34* | (2006.01) |
| *C12M 3/00* | (2006.01) |
| *C12Q 1/68* | (2006.01) |
| *B01L 7/00* | (2006.01) |

(52) U.S. Cl.
CPC ................. *C12Q 1/6869* (2013.01); *B01L 7/52* (2013.01); *B01J 2219/00722* (2013.01); *B01J 2219/00659* (2013.01)
USPC ........................ 435/287.2; 435/6.1; 422/82.08

(58) Field of Classification Search
CPC ............. B01J 2219/00722; B01J 2219/00659; B01L 7/52; B01L 2300/0636; C40B 40/06; G01N 21/6428; G01N 21/645; G01N 21/643; G01N 21/648; G01N 2021/6421
USPC ................... 435/6, 287.2; 422/82.08
See application file for complete search history.

(56) References Cited

U.S. PATENT DOCUMENTS

| | | | |
|---|---|---|---|
| 4,598,049 A | * | 7/1986 | Zelinka et al. ................. 422/116 |
| 4,815,916 A | * | 3/1989 | Beck ........................... 414/796.5 |
| 4,863,849 A | | 9/1989 | Melamede |

(Continued)

FOREIGN PATENT DOCUMENTS

| | | |
|---|---|---|
| JP | 3510272 B2 | 1/2004 |
| JP | 2007-97471 A | 4/2007 |

(Continued)

OTHER PUBLICATIONS

Kambara et al., Multiple-sheathflow capillary array DNA analyser, Nature, vol. 361, Feb. 11, 1993, pp. 565-566.

(Continued)

*Primary Examiner* — Michael Hobbs
(74) *Attorney, Agent, or Firm* — Mattingly & Malur, PC

(57) ABSTRACT

Accurate and sensitive sequencing in pyrosequencing is achieved by allowing complementary strand synthesis reaction to proceed homogeneously and completely in a short time while performing luminescence reaction for a sufficiently long time. DNA as a sequencing target is immobilized on the surface of a solid support. Nucleic acid substrates are injected from a dispenser to the support site where complementary strand synthesis is in turn performed rapidly and completely in a short time under a small reaction volume. Next, the support together with the product thereon is moved into a luminescence reaction solution where luminescence reaction is in turn performed. Thus, a DNA complementary strand synthesis reaction site and a luminescence reaction site are completely separated. The support surface is also washed by dipping the support in the luminescence reaction solution that contains a luminescence reagent and an enzyme that degrades redundant nucleic acid substrates.

11 Claims, 13 Drawing Sheets

(56) References Cited

U.S. PATENT DOCUMENTS

| | | | |
|---|---|---|---|
| 4,971,903 | A | 11/1990 | Hyman |
| 6,210,891 | B1 | 4/2001 | Nyren et al. |
| 6,258,568 | B1 | 7/2001 | Nyren |
| 6,840,733 | B2 * | 1/2005 | Bjorn et al. ................ 414/794.4 |
| 2006/0141494 | A1 * | 6/2006 | Kambara et al. .................. 435/6 |
| 2007/0054283 | A1 * | 3/2007 | Kishimoto et al. ............... 435/6 |
| 2007/0166729 | A1 * | 7/2007 | Kambara et al. .................. 435/6 |
| 2008/0274512 | A1 * | 11/2008 | Squirrell et al. ............. 435/91.2 |
| 2009/0142767 | A1 * | 6/2009 | Taniguchi et al. ................ 435/6 |

FOREIGN PATENT DOCUMENTS

| | | |
|---|---|---|
| WO | 98/13523 A1 | 4/1998 |
| WO | 2005/003375 A2 | 1/2005 |

OTHER PUBLICATIONS

Zhou et al., Miniaturized pyrosequencer for DNA analysis with capillaries to deliver deoxynucleotides, Electrophoresis 2001, vol. 22, pp. 3497-3504.

Hyman, A New Method of Sequencing DNA, Analytical Biochemistry, vol. 174, 1988, pp. 423-436.

Ronaghi et al., Real-Time DNA Sequencing Using Detection of Pyrophosphate Release, Analytical Biochemistry, vol. 242, 1996, pp. 84-89.

Zhou et al., Enzyme System for Improving the Detection Limit in Pyrosequencing, Analytical Chemistry, vol. 78, No. 13, Jul. 1, 2006, pp. 4482-4489.

Margulies et al., Genome sequencing in microfabricated high-density picolitre reactors, Nature, vol. 437, No. 15, Sep. 2005, pp. 376-380.

* cited by examiner

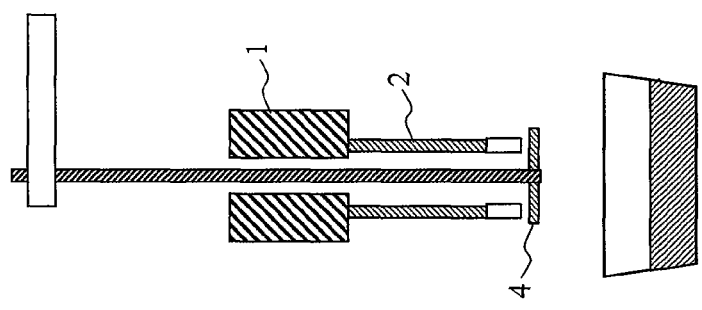
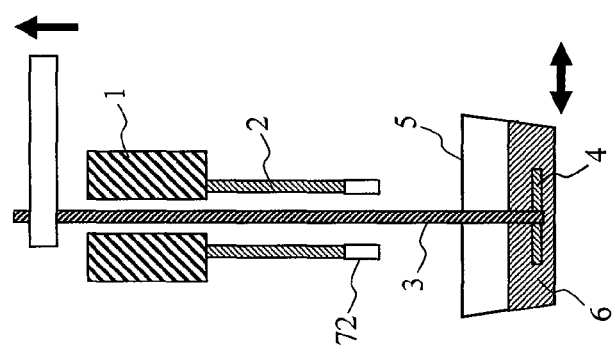
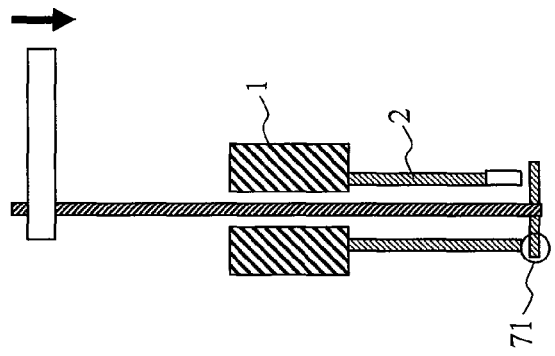
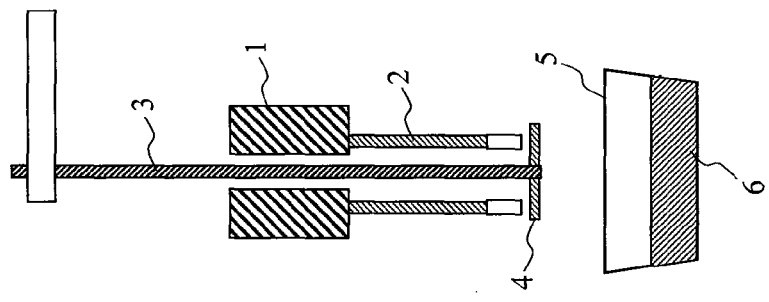

FIG. 14
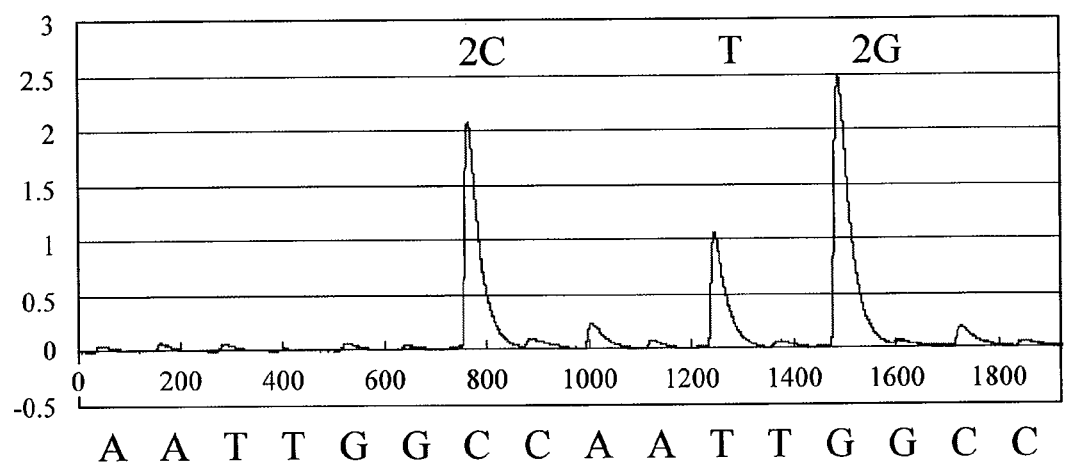
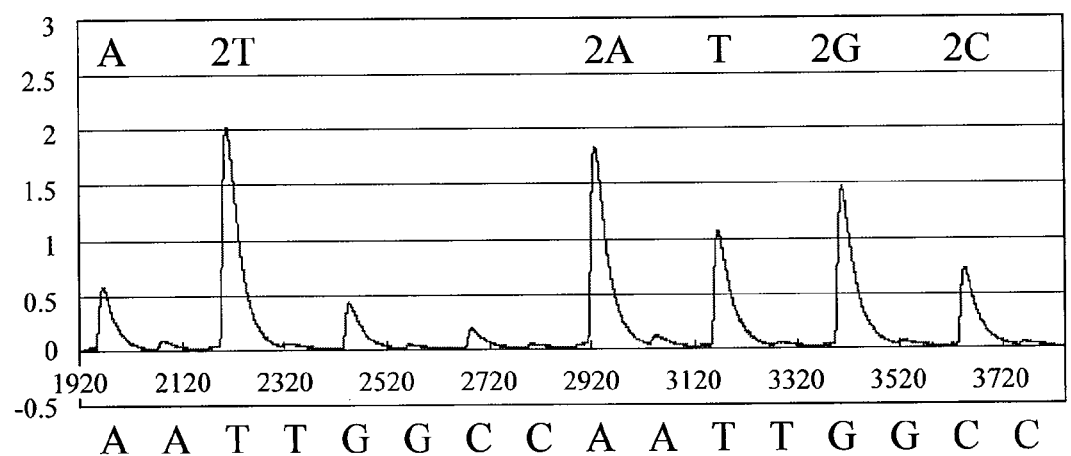

241

DNA ANALYSIS APPARATUS

CLAIM OF PRIORITY

The present application claims priority from Japanese patent application JP 2008-100592 filed on Apr. 8, 2008, the content of which is hereby incorporated by reference into this application.

BACKGROUND OF THE INVENTION

1. Field of the Invention

The present invention relates to DNA analysis and genetic diagnostics apparatuses such as an apparatus for sequencing the nucleotide sequence of DNA or identifying the types of nucleotides in DNA.

2. Background Art

Current methods for DNA sequencing used widely utilize gel electrophoresis and fluorescence detection. In this method, first, a large number of copies of a DNA fragment to be sequenced are prepared. Fluorescently labeled fragments with varying lengths starting at the 5' end of the DNA are prepared. The fluorescent labels added to these DNA fragments differ in wavelength according to the type of a 3'-terminal nucleotide thereof. The difference by one nucleotide in length is distinguished by gel electrophoresis. Luminescence produced by each fragment group is detected. The types of the terminal nucleotides of the DNA fragment groups during measurement are determined based on their respective luminescence wavelengths. The DNA fragment groups pass, in order of increasing length, through a fluorescence detection part. Therefore, by measuring fluorescence color, the types of the terminal nucleotides of the DNA fragment groups can be determined in order of increasing length. As a result, the sequence of interest is determined. Such fluorescent DNA sequencers have been widely diffused and have played an important role in the human genome analysis (see Nature, Vol. 361, 565-566, 11 Feb. 1993). On the other hand, as announced in 2003, the humane genome sequencing has been completed. Now, sequence information is exploited in medical care or various industries. In these fields, long DNA does not have to be completely sequenced, and the determination of a short DNA sequence of interest is adequate in most cases. For this purpose, convenient and inexpensive apparatuses are required. Furthermore, the simultaneous sequencing of a very large number of DNA fragments has been increasingly demanded. For such DNA sequencing, convenient and extensible methods and apparatuses are required.

In response to these demands, techniques typified by pyrosequencing have been developed, which achieve sequencing through stepwise chemical reaction. In this method, primers are hybridized to a target DNA strand, and four nucleic acid substrates (dATP, dCTP, dGTP, and dTTP) for complementary strand synthesis are sequentially added one by one into a reaction solution where complementary strand synthesis reaction is in turn performed. Once the complementary strand synthesis reaction occurs, a DNA complementary strand extends to produce pyrophosphoric acid (PPi) as by-products. The pyrophosphoric acid is converted to ATP by the action of an enzyme coexisting therewith. This ATP reacts in the presence of luciferin and luciferase to produce luminescence. By detecting this light, the incorporation of the added substrate for complementary strand synthesis into the DNA strand is determined. As a result, the sequence information of the complementary strand, thus the sequence information of the target DNA strand, is determined (see Electrophoresis, 22, 3497-3504 (2001)). The original method of pyrosequencing was as follows (see U.S. Pat. No. 4,863,849): DNA was immobilized at some midpoint of a column, and a solution containing substrates for complementary strand synthesis was allowed to run in the column such that the reaction product pyrophosphoric acid passed through several reaction parts. In this process, the pyrophosphoric acid was converted to ATP, which then produced luminescence by use of a luciferin-luciferase luminescence system, and this luminescence was detected (see Analytical Biochemistry 174, 423-436 (1988)).

On the other hand, in a method disclosed by Nyren et al., substrates for complementary strand synthesis unused in the reaction were immediately degraded by use of an enzyme such as apyrase to eliminate the influence on next reaction step (see U.S. Pat. Nos. 4,971,903 and 6,258,568). This method may be achieved merely by sequentially adding reagents to a reaction chamber and is therefore more convenient. In the luciferin-luciferase luminescence system, not only ATP, but also dATP serving as a substrate for complementary strand synthesis, acts as a luminescent substrate. Thus, its analog dATP$\alpha$S, which does not serve as a luminescent substrate, is used (see U.S. Pat. No. 6,210,891, JP Patent No. 3510272, and Analytical Biochemistry 242, 84-89 (1996)).

The present inventors have developed a method for highly sensitively examining a DNA sequence with less background luminescence, which comprises the process of producing ATP from pyrophosphoric acid and AMP using PPDK, instead of ATP sulfurylase conventionally used, as an enzyme involved in ATP-producing reaction from pyrophosphoric acid (see JP Patent Publication (Kokai) No. 2007-097471A (2007) and Analytical Chemistry, 78, 4482-4489, (2006)).

This method is also suitable for the parallel sequencing of many DNA samples. An attempt has been reported to sequence DNA samples in parallel by use of several tens of thousands to several millions of reaction cells (see WO2005/003375 and Nature, 437, 376-380 (2005)).

SUMMARY OF THE INVENTION

In pyrosequencing, a DNA sequence is determined by detecting luminescence using stepwise complementary strand synthesis reaction and chemical luminescence reaction. The originally reported method of pyrosequencing involves performing complementary strand synthesis and chemical luminescence reactions in different reaction chambers. Specifically, a reaction solution containing pyrophosphoric acid produced by complementary strand synthesis and redundant nucleic acid substrates was moved from the complementary strand synthesis reaction chamber to another reaction chamber where luminescence reaction was in turn performed. An alternative method previously reported involves: degrading redundant nucleic acid substrates in this reaction solution by allowing the solution to pass, on its way to a chemical luminescence reaction chamber, through a region on which an enzyme that degrades the substrates is immobilized; then converting pyrophosphoric acid to ATP; and leading the resultant solution to the chemical luminescence reaction chamber. However, this method required a complicated procedure in which the complementary strand synthesis reaction solution was washed for every addition of nucleic acids and replaced by a new solution. Thus, a newly proposed, convenient method has been diffused, which comprises allowing complementary strand synthesis reaction, degradation reaction of redundant nucleic acid substrates, ATP-producing reaction, and luminescence reaction to coexist.

However, this approach has various disadvantages due to the unstable reaction system in which complementary strand synthesis reaction using dNTPs as substrates coexists with degradation reaction for removing dNTPs. In the presence of a large amount of degrading enzymes, dNTPs disappear prior to sufficient completion of complementary strand synthesis reaction, and unreacted DNA templates remain in the reaction solution. Such templates accumulate through every stepwise reaction and eventually produce extended complementary strands having various ends formed by complementary strand synthesis. As a result, sequencing is unsuccessful, which is conducted based on luminescence derived from ATP converted from pyrophosphoric acid obtained by stepwise complementary strand synthesis reaction. Specifically, due to the various ends formed by complementary strand synthesis, any of nucleic acid substrates injected cause partial complementary strand synthesis. As a result, signals are always observed. On the other hand, in the presence of a small amount of degrading enzymes, nucleic acid substrate dNTPs are injected prior to complete degradation of nucleic acid substrates used in preceding complementary strand synthesis. Thus, a mixture of these substrates exists in the reaction cell where many complementary strand synthesis reactions in turn proceed at a time. After all, complementary strand synthesis products having various lengths are formed, disadvantageously resulting in unsuccessful DNA sequencing. To avoid this, nucleic acid substrates must be injected at long time intervals. However, this approach consumed too much time and was thus unpractical.

Furthermore, a nucleic acid substrate dATP, which is structurally analogous to ATP, serves as a substrate for luciferase reaction. Therefore, dATP produces chemiluminescence with unignorable intensity, albeit much weaker than that produced by ATP, in sequencing reaction using a reaction system also containing degrading enzymes. Specifically, dATP slightly produces luminescence through immediate reaction with luciferase while producing pyrophosphoric acid, in a period from the production of pyrophosphoric acid by dATP in complementary strand synthesis reaction, through ATP synthesis, to the detection of signals produced through luciferase-catalyzed luminescence reaction. The produced pyrophosphoric acid is converted to ATP by an enzymatic cycle. This ATP in turn contributes to luminescence reaction again. dATP serving as a substrate for complementary strand synthesis reaction must be added in a much larger amount to a reaction chamber than that of luminescence signal-producing ATP formed from pyrophosphoric acid produced by complementary strand synthesis. For this reason, together with the reaction interval, dATP gave relatively large luminescence in the conventional reaction system and was a barrier to measurement. Thus, instead of dATP, dATPαS, which is available in DNA complementary strand synthesis without serving as a substrate for chemiluminescence reaction, is used as a substrate for complementary strand synthesis. However, this reagent is more expensive than dATP and is far inferior to dATP in properties (e.g., reaction rate) as a substrate for complementary strand synthesis. Therefore, dATPαS must be added in large amounts in reaction. Thus, the development of a method directly using dATP has been demanded.

To solve the problems, the present invention is intended to spatially separate a complementary strand synthesis reaction site and a luminescence reaction site. Moreover, the present invention adopts a method which comprises: after the completion of complementary strand synthesis reaction, dipping the complementary strand synthesis reaction site in a luminescence reaction solution having an amount 10 times or larger that of the complementary strand synthesis reaction solution; and performing luminescence reaction.

Specifically, a DNA analysis apparatus according to the present invention comprises: a holding member which holds a DNA sample; a substrate supplying part which individually supplies plural types of substrates for complementary strand synthesis to the DNA sample held by the holding member; a reaction vessel which accommodates a reaction solution that produces luminescence through reaction with a DNA complementary strand synthesis reaction product; a photodetector which detects luminescence produced in the reaction solution; and a controlling part which controls the position of the holding member as well as the supply of the substrates for complementary strand synthesis from the substrate supplying part, wherein the controlling part positions the holding member outside the reaction solution in the reaction vessel to perform the supply of the substrates for complementary strand synthesis from the substrate supplying part and then moves the holding member into the reaction solution in the reaction vessel. The holding member that can be used is a membrane, string-like member, beads, or magnetic beads.

According to the present invention, complementary strand synthesis reaction can proceed using a small volume of a reaction solution and high concentrations of enzymes and reagents involved in the complementary strand synthesis. Therefore, the complementary strand synthesis reaction can be done almost completely in a short time. A degrading enzyme apyrase is absent at a site containing template DNA. Therefore, the complementary strand synthesis reaction can proceed fully in a short time without competing with degradation reaction of substrates. Redundant dNTPs, particularly, dATP, are degraded by the addition of a degrading enzyme apyrase after complementary strand synthesis reaction or by moving these substrates through diffusion to an apyrase-immobilized region. Alternatively, apyrase may be added in advance to a luminescence reaction part where dNTP degradation reaction is in turn performed in parallel with luminescence reaction. In this case, even degradation that consumes a certain amount of time has neither practical problem nor influence on complementary strand synthesis. The complementary strand synthesis site containing the reaction product is dipped in a luminescence reaction solution in larger excess than the complementary strand synthesis reaction solution. Pyrophosphoric acid contained therein is converted to ATP, which is in turn used in luminescence reaction. Alternatively, the apyrase-immobilized region may be brought into contact with the reaction solution prior to luminescence reaction. In this case, dATP, which has already been degraded, does not give large background luminescence. Thus, highly sensitive and accurate sequencing can be achieved by virtue of complete complementary strand synthesis and full luminescence reaction. The present invention further has the advantage that dATP, which has been difficult to use so far, can be exploited directly as a substrate for complementary strand synthesis.

BRIEF DESCRIPTION OF THE DRAWINGS

FIG. 6 is a diagram showing a state in which dNTPs are uninjected.

FIG. 7 is a diagram showing a state in which dNTPs have been injected.

FIG. 8 is a diagram showing a state in which a movable stage is lowered such that a membrane is dipped in a reaction vessel which is vibrated.

FIG. 9 is a diagram showing a state in which a movable stage is raised such that a membrane is taken out of a reaction vessel.

FIG. 14 is a diagram showing an example of DNA sequencing according to the present invention.

Figure 1:
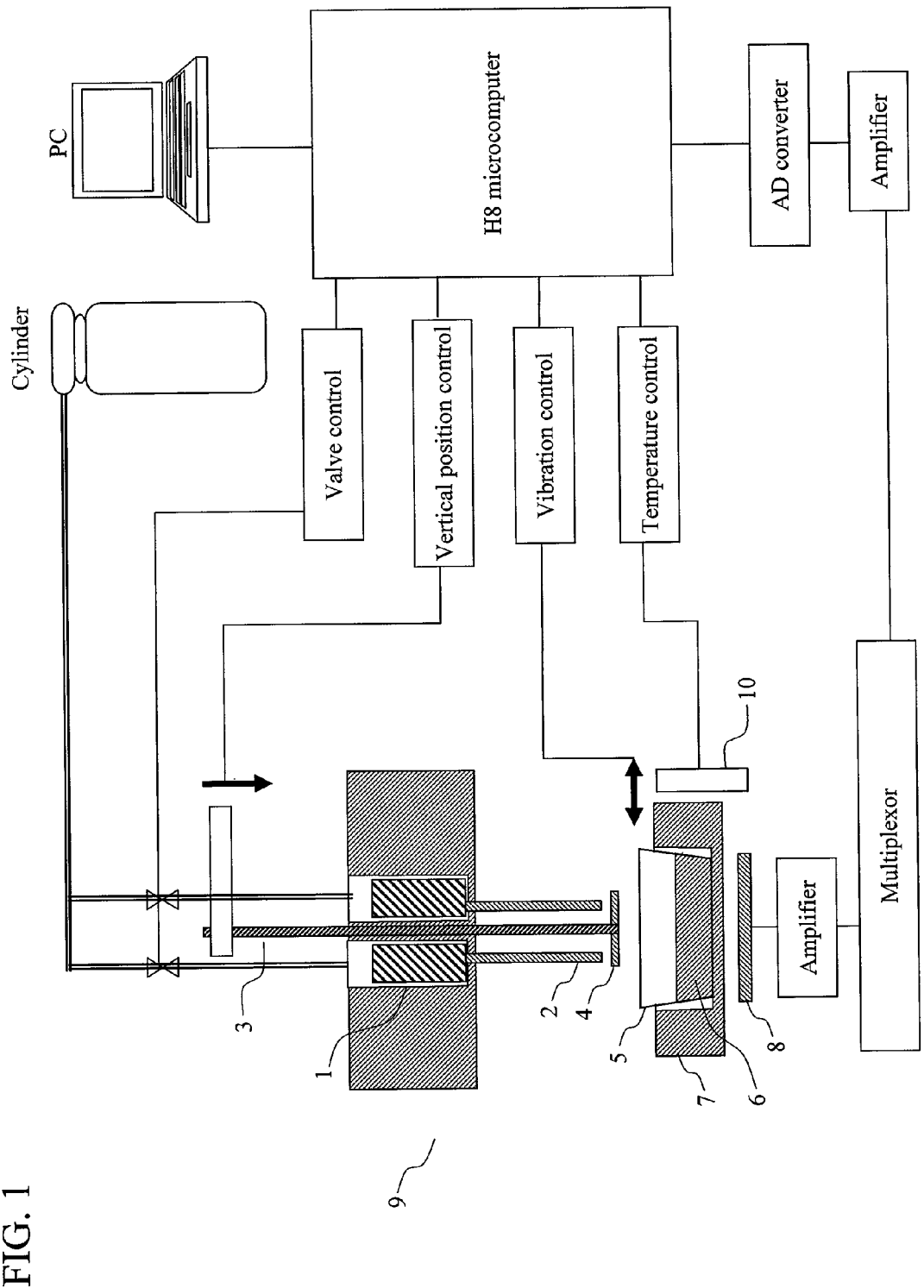
FIG. 1 is a diagram showing the overall structure of an apparatus comprising a membrane with a micro region disposed in a movable stage.

DESCRIPTION OF REFERENCE NUMERALS 1 dispenser
2 capillary
3 movable stage
4 membrane
5 reaction vessel
6 luminescence reagent
7 reaction vessel holder
8 photodiode
9 dispenser holder
10 Peltier device
71 injected dNTP
72 air gap
101 O-ring
111 squeezing jig
121 heater
171 string
172 template DNA-immobilized part
173 apyrase-immobilized part
174 string support
175 washing solution influent tube
176 washing solution effluent tube
177 absorber
181 template DNA-immobilized membrane
182 apyrase-immobilized membrane
191 template DNA-immobilized beads
192 magnet
201 micropillar
202 beads
211 magnet
212 template DNA-immobilized beads
213 holding rod
241 wire holder for holding beads

DETAILED DESCRIPTION OF THE PREFERRED EMBODIMENTS

Hereinafter, embodiments of the present invention will be described with reference to the drawings.

Example 1

The present Example relates to a method which comprises: attaching a DNA-immobilized membrane to a movable stage; moving up and down the movable stage such that DNA templates and reaction products are moved between a complementary strand synthesis position and a luminescence reaction position; and conducting DNA sequencing or DNA analysis. Various membranes such as filter papers and nylon filters can be used.

Figure 2:
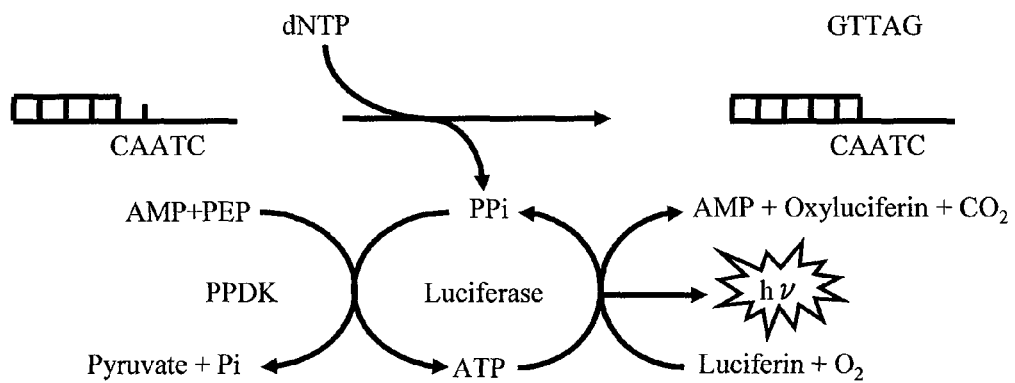
FIG. 2 is a diagram showing the principle of stepwise sequencing.
Figure 3:
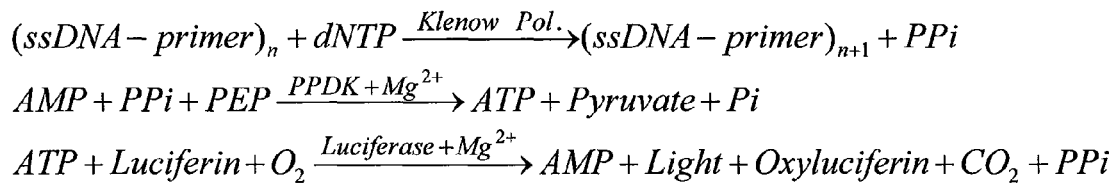
FIG. 3 is a diagram showing enzymatic reaction in stepwise sequencing.

FIG. 2 shows reaction associated with pyrosequencing according to the present invention as well as the principle of the sequencing. FIG. 3 shows a process involved in luminescence reaction. Conventional ATP-producing reaction subsequent to complementary strand synthesis reaction utilizes ATP sulfurylase and APS. By contrast, the reaction system adopted here utilizes PPDK (pyruvate phosphate dikinase), AMP, and PEP (phosphoenolpyruvic acid). The present invention can be applied to both the reaction systems.

In pyrosequencing, primers are hybridized to target DNA. After the addition of DNA polymerase, four nucleic acid substrates (dNTPs: dATP, dCTP, dGTP, and dTTP) are sequentially added into the reaction solution where complementary strand synthesis reaction is in turn performed. Pyrophosphoric acid produced as by-products during the complementary strand synthesis is converted to ATP through the reaction shown in FIG. 3. This ATP is reacted with luciferin in the presence of luciferase to produce luminescence. Once the complementary strand synthesis occurs, pyrophosphoric acid is produced, ending in the production of luminescence. By monitoring this light, the occurrence of complementary strand synthesis, i.e., the type of the incorporated nucleotide, is determined. As a result, the target DNA sequence is determined.

In the originally proposed method of pyrosequencing, a reaction region and a luminescence region were connected via a pipe. DNA was immobilized on a complementary strand synthesis region, while luciferase involved in luminescence reaction was immobilized on a luminescence reaction region. A reaction solution underwent degradation of redundant dNTPs (dATP serves as a substrate, albeit weak, for luciferase reaction and is therefore preferably removed) on its way to the luminescence reaction part and was then transferred to the luminescence reaction region where luminescence reaction was in turn performed.

This method had complicated procedures and exhibited insufficient performance. Thus, Nyren et al. have made a modification thereto. Specifically, one reaction region is prepared where DNA complementary strand synthesis reaction, degradation reaction of redundant dNTPs using a degrading enzyme apyrase, ATP-producing reaction from pyrophosphoric acid, and luciferin-luciferase luminescence reaction using ATP are performed simultaneously. This method has exceedingly simple procedures and may be achieved merely by sequentially adding nucleic acid substrates to the reaction region. This method has captured great attention and has advanced as practical sequencing. However, many enzymatic reactions are performed simultaneously. Therefore, each reaction may fail to fully proceed and thus has adverse effects on the method. Particularly, the nucleic acid substrates used in complementary strand synthesis reaction are degraded concurrently by use of apyrase. Fast degradation leaves DNA strands that miss their complementary strand synthesis. Such DNA strands disturb the complementary strand synthesis phase (the progress of DNA complementary strand synthesis) and eventually make sequencing difficult. On the other hand, the nucleic acid substrates may be degraded slowly and remain until next injection of nucleic acid substrates. In this case, both the newly added and residual nucleic acid substrates are disadvantageously incorporated in complementary strand synthesis to accelerate the reaction too much. The optimum conditions for the enzymatic reactions used here differ from reaction to reaction. When all the reactions are performed in one reaction region, it is almost impossible to simultaneously optimize all the reactions. Moreover, the volume of the reaction region must be large to some extent, for example, for securing luminescence intensity. Therefore, disadvantageously, complementary strand synthesis hardly proceeds homogeneously.

To solve these problems, in the method of the present Example, complementary strand synthesis reaction is confined to a region with a small volume on a membrane, and the reaction products are transferred to a luminescence reaction region without separating from the DNA templates. Specifically, complementary strand synthesis proceeds rapidly and homogeneously in a state separated from other reactions using a small volume, thus a high substrate concentration, while the washing of the reaction part (degradation of redundant dNTPs), ATP production, and luciferase reaction are performed in a luminescence reaction region. By separating these regions, each reaction can be performed under more optimum conditions.

First, the outline of an apparatus of the present Example will be described with reference to FIG. 1. In the present Example, a small region of complementary strand synthesis is set to a membrane 4. By moving up and down this membrane 4, a product obtained in the complementary strand synthesis reaction part is sent to a luminescence detection part. dNTPs are injected from a dispenser 1 held by a dispenser holder 9 via a capillary to the membrane 4 where the complementary strand synthesis of the DNA immobilized thereon is in turn performed. Next, the membrane 4 is moved by a movable stage 3 into a solution in a reaction vessel 5 serving as a luminescence reaction region. The movable stage is moved by an up-and-down movement motor. Luminescence reaction occurs in the reaction vessel, and the luminescence is detected by a photodiode (Si photodiode S1133-01, manufactured by Hamamatsu Photonics K.K.) 8. The photodiode converts light with $10^{-6}$ to $10^5$ lux to a current with $10^{-14}$ to $10^{-3}$ A and has linearity over a range as exceedingly wide as 11 digits. The photodiode permits measurement even in full sunlight (1000 lux) without being broken. A usual signal level is $10^{-4}$ lux and can therefore be measured sufficiently by the photodiode.

The apparatus comprises plural photodiodes corresponding to plural reaction vessels. The obtained signal is amplified by an amplifier (opA129UB, manufactured by Texas Instruments Inc.) directly coupled to each photodiode and then transmitted to a multiplexor (MAX4051ACSE, manufactured by Maxim Integrated Products, Inc.). The plural signals are time-divided and AD-converted. Prior to the AD conversion, the signals are amplified through an amplifier into necessary signal intensity. A gain is automatically set to 3 levels, ×1, ×10, and ×100, for amplification (op07CS, manufactured by Analog Devices, Inc.). The signals converted to digital signals by an AD converter (ADS1271PW, manufactured by Texas Instruments Inc.) are processed by an H8 microcomputer (HD64F3052BF25, manufactured by Renesas Technology Corp.) and output to a personal computer (PC). The H8 microcomputer performs valve control, vertical position control for the movable stage 3, vibration motor control to stir a luminescence reagent 6 in the reaction vessel 5, and temperature control. The amount of dNTPs injected by the dispenser 1 is controlled based on valve opening/closing timing by applying air pressure thereto from a cylinder or piping installed therein. The movable stage 3 is driven by the up-and-down movement motor. Temperature adjustment is performed by heating/cooling a reaction vessel holder 7 by a Peltier device 10.

The membrane 4 had a round shape of 3 mm in diameter. However, the size and the shape are not limited thereto. The membrane used here was SAM2(R) Biotin Capture Membrane (manufactured by Promega Corp., catalog No. V7861), which is a membrane coated with streptavidin through covalent bond. Dispensers 1 respectively have 200-μL reservoirs that correspond to four substrates and comprise, at the ends thereof, capillaries 2 of 360 μm in outer diameter and 50 μm in inner diameter made water repellent. A 1-mm hole penetrates the center of the four reservoirs. The movable stage 3 runs through this through-hole at the central part of the dispensers.

The gap between the end of the capillary 2 and the membrane 4 is set to sufficiently spread droplets onto the membrane but prevent unnecessary dNTPs from leaking. As an example, this gap is set to 0.5 mm±0.2 mm. Such a setting spreads dNTP droplets onto the membrane from the capillary without problems when 2.3 μL of dNTPs is supplied. The size of the gap may be up to 0.9 mm±0.2 mm. For 1 μL of the dNTP solution, the size of the gap is 0.5 mm±0.2 mm at the maximum. For a smaller amount of the dNTP solution, the gap must be rendered narrower to enhance accuracy.

Figure 4:
FIG. 4 is a diagram showing a state in which a membrane is unattached.
Figure 5:
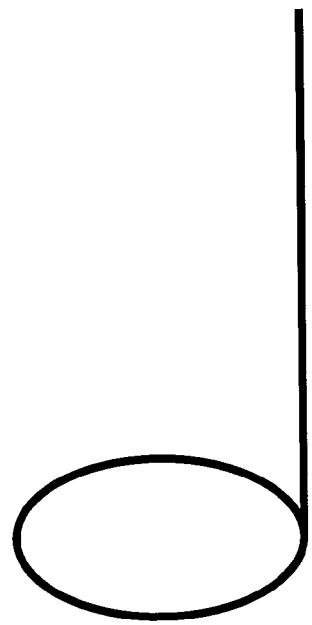
FIG. 5 is a diagram showing a state in which a membrane has been attached to a holder.

Up to this point, the method for setting the gap between the capillary and the membrane has been described. Alternatively, a transparent thin plate may be placed as a reinforcement below the undersurface of the membrane to enhance gap accuracy. Alternatively, the membrane may be fit, for use, into holding frames as shown in FIG. 4. FIG. 4 shows an example of a scheme in which the membrane is sandwiched by two rings. FIG. 5 is a diagram showing a state in which the membrane has been attached to a holder.

Alternatively, the leakage of dNTPs can also be prevented by reducing pressure within the reservoir and providing an air gap at the tip of the capillary. First, the capillary 2 at the end of the dispenser 1 is brought close to the membrane 4 (FIG. 6), and dNTPs are injected (FIG. 7). As shown in FIG. 6, the capillary of the dispenser has an air layer at the tip thereof. As shown in FIG. 7, the nucleic acid substrates are supplied onto the membrane surface from the capillary injecting them. The other capillaries have no change. The injected dNTPs 71 are spread onto the membrane 4. Then, this state is kept, and then, the movable stage 3 is lowered such that the membrane 4 is dipped in the luminescence reagent 6 in the reaction vessel 5 (FIG. 8). The reaction vessel 5 is vibrated to smoothly promote luminescence reaction. While the capillary 2 at the end of the dispenser is away from the membrane 4, pressure within the reservoir of the dispenser is reduced, and an air gap layer 72 is provided at the tip of the capillary. Luminescence reaction proceeds, and then, signals are sufficiently attenuated by apyrase. Therefore, the movable stage 3 is raised and put on standby until next injection (FIG. 9).

Figure 10:
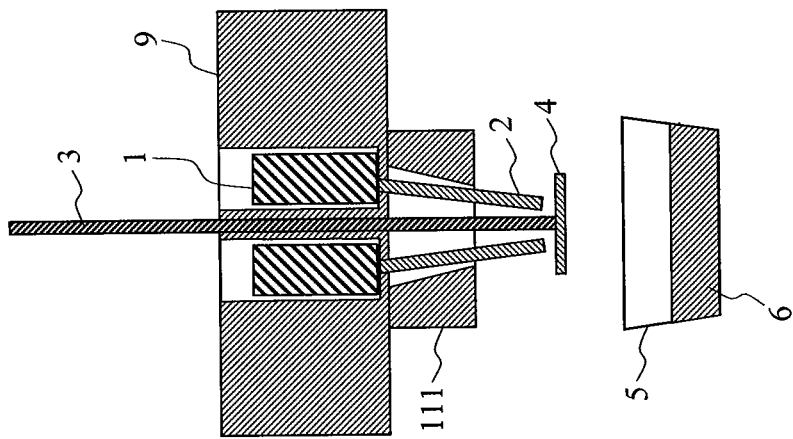
FIG. 10 is a diagram showing a state in which capillaries are squeezed by an O-ring.
Figure 11:
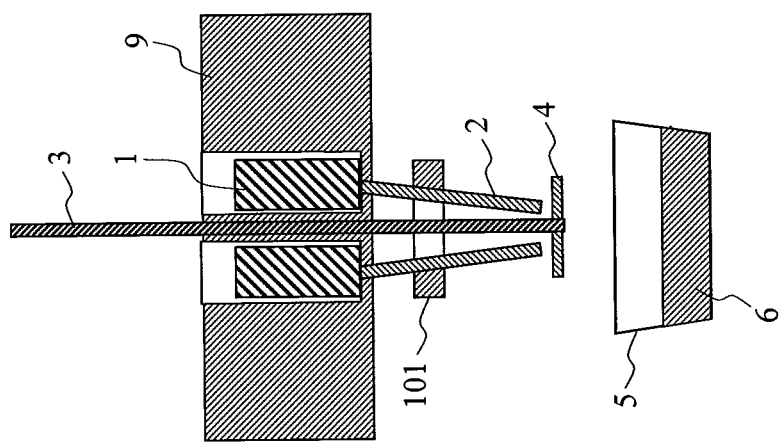
FIG. 11 is a diagram showing a state in which capillaries are squeezed by a squeezing jig.

The capillary of each dispenser is placed such that its tip is positioned 0.5 to 1 mm above the membrane of 3 mm in diameter. The dispenser holder 9 may optionally comprise an O-ring 101 as shown in FIG. 10 or a jig 111 functionally similar thereto as shown in FIG. 11. In this case, the capillaries 2 are squeezed such that their tips are positioned above the membrane of 3 mm in diameter.

Here, the DNA was immobilized onto the membrane by a method using biotin-avidin bond. However, the immobilization method is not limited thereto.

```
TPMT-R2 primer:
                                           (SEQ ID NO: 1)
5'-a aaat tact tacc attt gcga tca-3' template DNA Bios1-R:
                                           (SEQ ID NO: 2)
5'-biotin-tttt tttt tttt tttt tttt ca ttag ttgc
catt aatc cagg tga tcgc aaat ggta agta attt tt-3'

Sequence to be analyzed:
                                           (SEQ ID NO: 3)
5'-cctg gatt aatg gcaa ctaa tg-3'
```

4 μL of template DNAs having a concentration of 1 μM, i.e., 4 pmol template DNAs, is injected to the membrane. According to the catalog, biotin-avidin bond requires 30 seconds or shorter. Therefore, 2 minutes later from the injection of the template DNAs, the membrane is washed with 2×C buffer. The composition of the 2×C buffer is 120 mM Tricine, 4 mM EDTA, and 40 mM MgAc$_2$. Next, the membrane is dipped in a solution containing 1 μL of polymerase enzyme Klenow injected into 60 μL of a luminescence reagent. Then, the membrane is washed with an Apy-PPase solution to remove ATP or PPi contained in the polymerase enzyme. The composition of the Apy-PPase is an aqueous solution having an apyrase concentration of 1 U/mL and a PPase concentration of 1 U/mL. After the washing with the Apy-PPase solution, the membrane is washed again with 2×C buffer.

The amount of the DNAs is 0.5 to 4 pmol. However, the amount is not limited thereto. This DNA-immobilized membrane is first placed above the luminescence reaction region. First nucleic acid substrates are supplied onto the membrane surface by a capillary glass tube or dispenser nozzle made of a microfabrication device from above the movable stage. The solution containing the nucleic acid substrates is spread in a short time on the small membrane where complementary strand synthesis reaction then starts. The amount of the substrates injected is 0.5 to 4 μL. However, the amount is not limited thereto. The concentration of the nucleic acid substrates is set to 125 μM each for dATPs, dCTPs, dGTPs, and dTTPs. However, the concentration is not limited thereto. The composition of a luminescence reaction solution is shown in Table 1.

TABLE 1

Composition of luminescence reagent

| Composition | Amount in 20 μL of luminescence reagent, Concentrations are provided within parentheses |
|---|---|
| Tricine | $1.2 \times 10^{-6}$ mol (60 mM) |
| EDTA | $4 \times 10^{-8}$ mol (2 mM) |
| MgAc | $4 \times 10^{-7}$ mol (20 mM) |
| Ultrapure water | 5.15 μL |
| PPDK | 300 mU (15 mU/μL) |
| Luciferase | 71.4 μg (60 μM) $1 \times 10^{10}$ LU |
| Luciferin | $8 \times 10^{-9}$ mol (400 μM) |
| PEP•3 Na | $1.6 \times 10^{-9}$ mol (80 μM) |
| AMP | $8 \times 10^{-9}$ mol (400 μM) |
| BSA | 20 nL |
| DTT | $4 \times 10^{-9}$ mol (200 μM) |
| Apyrase | 24 mU (1.2 mU/μL) |

Once the complementary strand synthesis occurs, some nucleic acid substrates are consumed to produce pyrophosphoric acid as by-products. The reaction proceeds rapidly and is therefore done almost completely a few seconds later. 10 seconds later from the reagent supply, the movable stage which holds the membrane is moved downward and sunk in a luminescence reaction chamber. The luminescence reaction chamber accommodates 100 μL (or around; the solution composition is more stable in the larger amount) of the reaction solution. The movable stage together with the DNA-immobilized membrane thereon is sunk into the solution. Components non-immobilized on the membrane, such as pyrophosphoric acid and redundant nucleic acid substrates, are immediately diffused and spread in the luminescence reaction solution where next reaction then proceeds. The movable stage may be moved slightly up and down such that the luminescence reaction solution is stirred to allow the reaction to proceed homogeneously. The pyrophosphoric acid on the membrane is diffused in the reaction solution and reacts with PPDK and AMP therein to produce ATP. On the other hand, in a system using ATP sulfurylase, pyrophosphoric acid reacts with APS to produce ATP. The ATP reacts with luciferin and oxygen in the presence of luciferase to produce luminescence. This light is measured by a photodetection element. The photodetection element used is an array sensor such as a photomultiplier, photodiode, or CCD. The redundant dNTPs on the membrane are diffused in the solution and converted, through degradation by a degrading enzyme such as apyrase, into a form that does not contribute to complementary strand synthesis reaction. The dipping of the membrane into the reaction solution also plays a role in washing the membrane surface. The membrane is dipped into the luminescence reaction solution and kept for approximately 1 minute in the solution. Then, the membrane is taken out thereof. The luminescence reaction solution adhering to the membrane does not affect subsequence complementary strand synthesis reaction.

Figure 12:
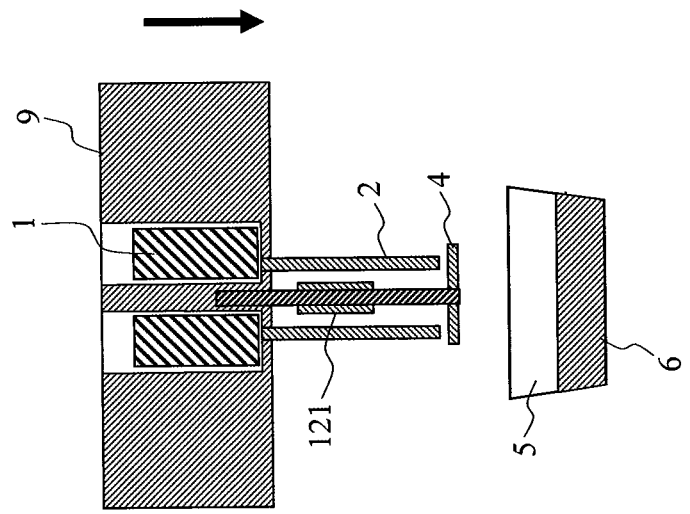
FIG. 12 is a sectional view showing a state in which a heater has been attached to a movable stage.

The optimum temperature of the complementary strand synthesis reaction is around 35° C. for Klenow used as the enzyme and is approximately 60° C. for a thermostable enzyme Thermo Sequenase DNA polymerase used as the enzyme. Therefore, as shown in FIG. 12, temperature control function is preferably imparted to the membrane-fixed holder by attaching a heater 121 thereto. The membrane taken out of the solution is used in a next reaction step. Specifically, next nucleic acid substrates are subsequently added thereto, and complementary strand synthesis reactions are sequentially performed.

Figure 13:
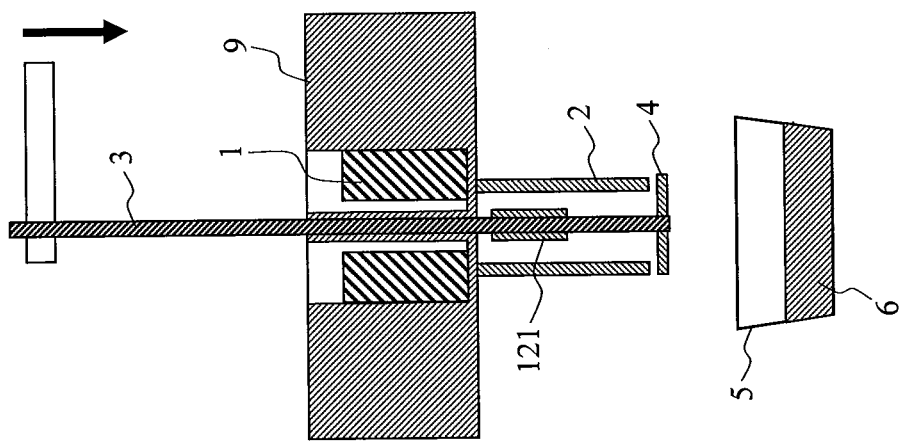
FIG. 13 is a sectional view showing a state in which a movable stage has been attached integrally to a dispenser holder.

In the present Example, the nucleic acid substrates were supplied from four dispensers disposed above and in proximity to the membrane. The dispensers 1 may be fixed at a relative position to the membrane 4, as shown in FIG. 13. Alternatively, the dispensers 1 may be fixed on the movable stage 3 to keep some distance from the membrane. In this case, the capillary 2 connected to the dispenser 1 is also sunk, together with the membrane 4, in the reaction solution 6 and however, works without any practical trouble as long as its tip is reliably made water repellent. On the other hand, the movable stage may comprise a hollow capillary such that nucleic acid substrates are supplied from the root in contact with the membrane. In this case, four nucleic acid substrates are sequentially supplied from reagent reservoirs, while a measure against contamination with residual reagents, such as the supply of a washing solution subsequent to the reagent injection, must be taken.

In the present Example, the DNA was biotinylated and immobilized on the membrane. Alternatively, a complex of target DNA and a primer may be captured, for use, by a DNA polymerase-immobilized membrane. An example of the obtained sequencing result is shown in FIG. 14. The abscissa represents an elapsed time as well as the types of injected nucleotides. The ordinate represents luminescence intensity. Luminescence occurs when the injected nucleotide is used in complementary strand synthesis. The incorporation of two molecules of the nucleic acid substrate per DNA produces luminescence intensity two times that produced by the incorporation of one molecule thereof. Therefore, the number of the nucleic acid substrate incorporated can be determined. From these pieces of information, the types of the incorporated nucleotides (nucleic acid substrates) are sequentially determined. As a result, the sequence of the template DNA can be read. A signal is sufficiently strong and is also proportional to the number of the incorporated nucleotide. Thus, it is demonstrated that the method of the present invention can achieve DNA sequencing.

Example 2

In the first Example, the removal of redundant nucleic acid substrates was achieved by adding apyrase into the luminescence reaction solution. This removal can also be achieved by immobilizing apyrase onto a site, of a membrane, different from a DNA-immobilized site. Specifically, in the second Example, degradation reaction of redundant nucleic acid substrates subsequent to complementary strand synthesis reaction can be performed by immobilizing template DNA onto a central part of the membrane and immobilizing apyrase onto a peripheral part thereof.

Figure 15:
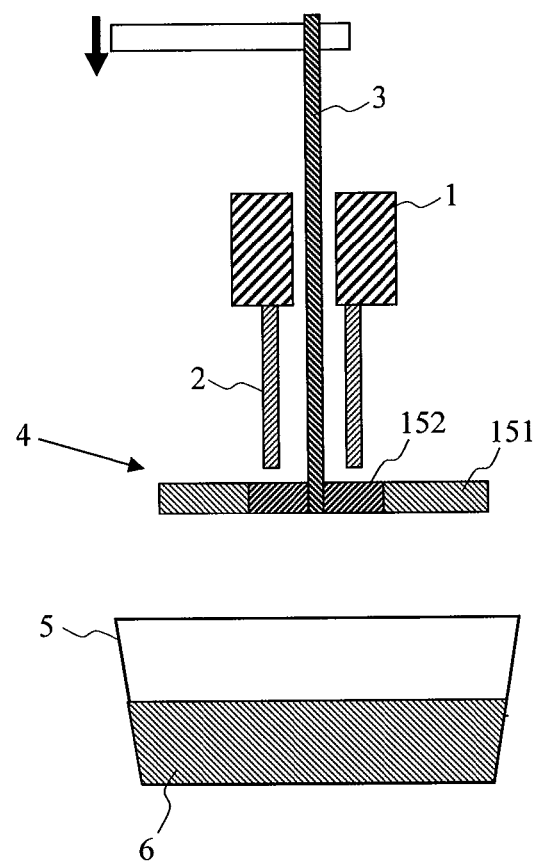
FIG. 15 is a sectional view of an apparatus comprising a membrane having an apyrase-immobilized peripheral part.
Figure 16:
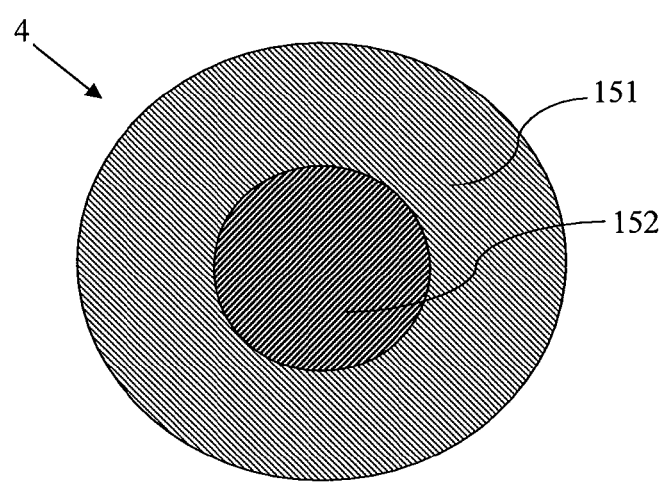
FIG. 16 is a top view of a membrane.

FIG. 15 shows the outline of an apparatus of the present Example. FIG. 16 is a top view of the membrane. Template DNA is immobilized on a region 152 in a central part of a membrane 4, while apyrase is immobilized on a region 151 in a peripheral part that surrounds the region 152. Nucleic acid substrates are supplied to a region in an almost central part of the membrane from a dispenser. The supplied nucleic acid substrates are first used in complementary strand synthesis reaction that occurs in the DNA-immobilized region 151 in the central part. The concentration of the nucleic acid substrates is set to a concentration higher than usual conditions for pyrosequencing. Therefore, the reaction is carried out rapidly and reliably. Subsequently, the nucleic acid substrates flow into the apyrase-immobilized region 151 where the redundant nucleic acid substrates are in turn degraded. A few seconds later from the injection of the nucleic acid substrates, a washing solution is also supplied from the same dispenser. In this case, the solution is supplied from the DNA-immobilized part to the apyrase-immobilized part. This structure has the effects of washing the dispenser and moving the nucleic acid substrates to the peripheral apyrase-immobilized region.

The reaction solution on the membrane 4 is put into a solution 6 containing a luminescence reagent where luminescence reaction is then performed in the same way as in Example 1. Apyrase may be added in advance to a luminescence reaction vessel 5. Alternatively, only a pyrophosphoric acid-degrading enzyme PPase may be added thereto. Luminescence reaction used in pyrosequencing serves as cyclical reaction by combining it with ATP-producing reaction. Therefore, the luminescence reaction alone continues until reaction substrates such as luciferin are exhausted. In this case, the PPase plays a role in degrading pyrophosphoric acid reproduced during the process such that the luminescence reaction is stopped after a given period of time. Of course, the luminescence reaction may also be stopped by degrading an intermediate product ATP by use of a small amount of apyrase added in advance. After the reaction, the membrane is taken out of the solution, and next complementary strand synthesis reaction is performed in the same way as in Example 1.

In the first and second Examples, the membrane, which has two-dimensional space, was used as a DNA-holding carrier. Alternatively, a string-like member, wire, or beads may be used as a DNA-holding carrier and may be fixed, for use, on the movable stage. In either case, a reaction reagent supply position and configuration are set such that the supplied reagents flow from the DNA-immobilized site to the apyrase-immobilized site.

Figure 17:
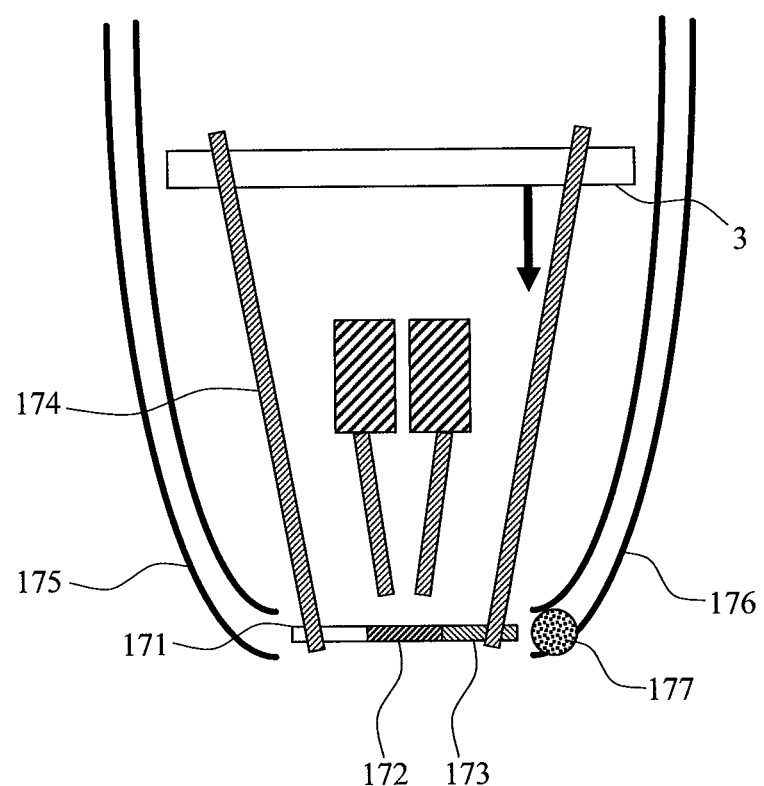
FIG. 17 is a sectional view of an apparatus in which a template DNA/apyrase-immobilized string is washed.

FIG. 17 shows an example in which a string-like member 171 is used as a DNA-holding carrier. In this case, DNA is immobilized on a central part 172 of the string held at both ends by string supports 174, while apyrase is immobilized on both end parts 173. A washing solution is supplied from a washing solution influent tube 175. For such a string, which has small ability to hold a solution, it is also effective to dispose a solution absorber 177 at the ends thereof such that the solution flows from the center toward the ends. The washing solution absorbed by the absorber 177 is discharged through a washing solution effluent tube 176.

In alternative configuration, DNA may be immobilized on one end of the string-like member, while apyrase may be immobilized on the other end thereof. In this case, a reaction solution containing nucleic acid substrates is moved from the DNA-immobilized side to the apyrase-immobilized side.

Example 3

In the second Example, the apyrase that degrades redundant nucleic acid substrates was immobilized on the DNA-immobilized membrane or string. In the present Example, DNA and apyrase are each independently immobilized on membranes or strings, which are then superposed to achieve the function of degrading redundant nucleic acid substrates unused in complementary strand synthesis.

Figure 18:
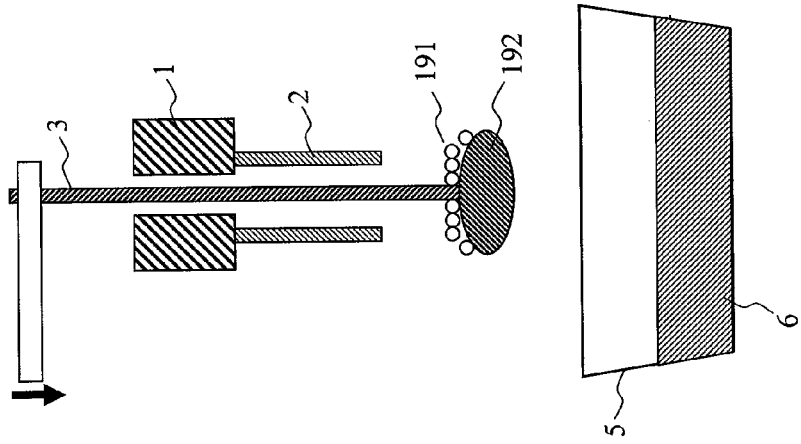
FIG. 18 is a sectional view of an apparatus in which membranes are superposed, one of which is an apyrase-immobilized membrane.

FIG. 18 shows the outline of an apparatus of the present Example. In the description below, membranes are taken as an example. A DNA-immobilized membrane 181 is superposed on an apyrase-immobilized membrane 182. These superposed membranes are placed in a movable stage 3. The DNA-immobilized membrane 181 is disposed in the upper part which is close to a dispenser 1, while the apyrase-immobilized membrane 182 is disposed in the lower part. Both the membranes may be superposed in advance for contact therebetween. Alternatively, a few seconds later from the supply of nucleic acid substrates, the space between the membranes may be lessened to bring them into contact with each other. In the description below, a state in which both the membranes have been brought in advance into contact with each other is taken as an example. In this example, nucleic acid substrates are sequentially supplied from four dispensers 1. Alternatively, other dispenser configurations may be used. The movable stage 3 is placed above a reaction chamber 5 which accommodates a luminescence reaction solution 6. Nucleic acid substrates are supplied onto the upper membrane 181 from the first dispenser. In the present Example, the membrane had an area of approximately 0.1 cm². However, the area is not limited thereto.

The nucleic acid substrates supplied onto the membrane are immediately spread on the membrane surface where DNA complementary strand synthesis reaction is in turn performed. The reaction itself is completed in a few seconds. The solution containing the nucleic acid substrates can also be moved through diffusion to the lower membrane 182. The nucleic acid substrates moved through diffusion to the lower membrane 182 are degraded by apyrase. This movement takes long. Therefore, time delay occurs between complementary strand synthesis and degradation reaction. As a result, sufficient complementary strand synthesis is secured, while the redundant nucleic acid substrates can be degraded. Such a small reaction region rapidly promotes the reaction. Therefore, the redundant nucleic acid substrates can be degraded almost fully by leaving them for 20 to 30 seconds. However, the reaction product pyrophosphoric acid is not degraded.

In usual pyrosequencing, dATP serves as a substrate for luminescence reaction and is therefore difficult or impossible to use. By contrast, in the present invention, a large majority of dATPs are degraded on their way to a luminescence reaction chamber and therefore, can be used. Unlike dATPαS usually used in pyrosequencing, dATP is an excellent substrate for complementary strand synthesis reaction and can perform complementary strand synthesis more smoothly. After the degradation reaction, the movable stage 3 is lowered and dipped in the luminescence reaction chamber 5 where ATP production and luciferase luminescence reaction are in turn performed. After the luminescence reaction for approximately 1 minute, the movable stage 3 is again taken out of the solution, and second nucleic acid substrates are added to the membrane where complementary strand synthesis reaction is then performed. These reactions are sequentially performed such that DNA complementary strand synthesis, luminescence reaction, and detection are repeated to achieve DNA sequencing.

Small molecules such as nucleic acid substrates can easily pass through the membrane and can therefore be moved through diffusion from the DNA-immobilized region to the apyrase-immobilized region. The membrane used here was 50 μm in thickness. However, the thickness is not limited thereto.

Example 4

In Examples 1 to 3, the membrane or string-like member was used as a DNA-holding material. In the present Example, an example in which DNA is immobilized on magnetic bead surface for operation will be described. The magnetic beads that can be used for DNA immobilization are as small as 1 to 30 μm. Alternatively, beads as large as 0.1 to 1 mm may be used. An example using large beads is described later in Example 5. Here, an example using small beads (2.8 μm Dynabeads) will be shown.

DNAs to be sequenced are immobilized on the bead surface. The immobilization was performed by use of a method which involves preparing biotinylated DNAs by PCR and immobilizing the DNAs onto avidin-labeled magnetic beads. However, the immobilization method is not limited thereto. The amount of the Dynabeads is approximately $10^6$ pieces per measurement. $10^6$ DNAs can be immobilized on one bead. Therefore, the amount of the DNAs used is approximately 1 pmol. The template DNAs immobilized on the magnetic beads are dipped in a solution containing DNA polymerases and primers such that the primers are hybridized thereto and the DNA polymerases are bound to the double-stranded parts. Subsequently, these beads are held by a very small magnet of 1 to 2 mm in diameter. The magnet is coupled to a thin movable stage and disposed above a luminescence reaction chamber by this movable stage. The magnet attached to the movable stage can be moved up and down and dipped in the luminescence reaction chamber.

Figure 19:
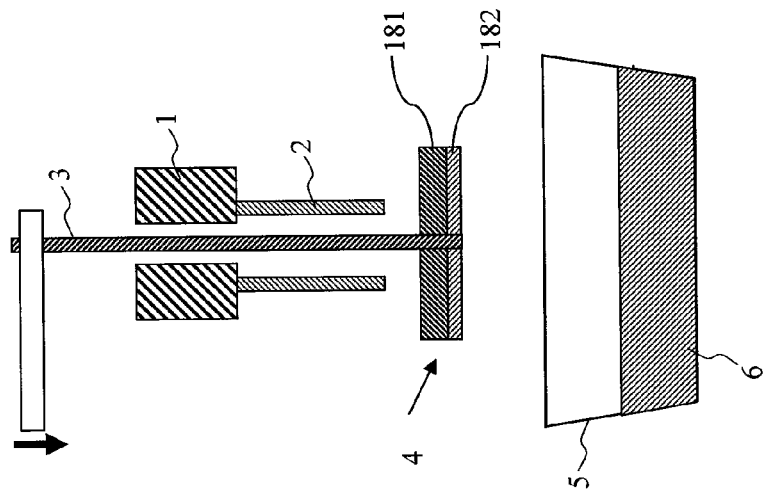
FIG. 19 is a sectional view of an apparatus comprising beads fixed on a magnet.

FIG. 19 shows a schematic diagram of an apparatus of the present Example. Magnetic beads 191 held on the surface of a magnet 192 fixed at the lower end of a movable stage 3 are first sunk in a luminescence reaction solution 6. Pyrophosphoric acid or ATP, if any, among DNAs causes unintended luminescence reaction. However, they disappear in a few minutes through apyrase degradation reaction. The movable stage 3 which holds the magnetic beads 191 is taken out of the luminescence reaction chamber 5 and stopped above the chamber. Four nucleic acid substrates used in complementary strand synthesis are sequentially supplied by dispensers 1 from above the magnet 192. First nucleic acid substrate dCTPs are initially supplied thereto. Once the complementary strand synthesis reaction occurs, pyrophosphoric acid is produced as by-products. However, no change is seen when this reaction does not occur. The magnetic beads 191 together with the DNA templates and the reaction product thereon are sunk in the luminescence reaction chamber. The produced pyrophosphoric acid, if any, is converted to ATP, which is in turn used in luciferase reaction. By detecting the light, the occurrence of complementary strand synthesis can be determined. Unreacted nucleic acid substrates are diffused into the reaction solution and degraded by apyrase within 1 to 2 minutes.

The magnet 192 attached to the movable stage 3 does not have to be kept in the luminescence reaction chamber 5 throughout luminescence reaction and can be taken out of the reaction solution 6 after the diffusion of the pyrophosphoric acid and redundant nucleic acid substrates on the surface into its surroundings. The magnet 192 may be vibrated up and down in the reaction solution 6. In this case, the magnet can be taken out of the solution in 5 to 10 seconds by virtue of fast diffusion. The DNAs, primers, and DNA polymerases immobilized on the magnetic beads 191 remain on the surface of the magnet 192 taken out thereof. Second nucleic acid substrate dGTPs are added to the surface of the magnet 192 such that the substrates for complementary strand synthesis are supplied to the magnetic beads 191. The same procedures as above are performed. Subsequently, nucleic acid substrates, dATPs, dTTPs, dCTPs, . . . are sequentially added, and measurement is repeated. Here, the dATP was added as a nucleic acid substrate. Alternatively, dATPαS may be used instead thereof.

The method of the present invention can perform complementary strand synthesis reaction at a fast reaction rate using a remarkably small reaction volume, thus nucleic acid substrate concentrations kept high, compared to a conventional scheme using a reaction system in which complementary strand synthesis reaction, ATP-producing reaction, degradation reaction of nucleic acid substrates, and luminescence reaction are all mixed. Therefore, the method of the present invention does not have to use nucleic acid substrates in excess relative to DNA templates. The nucleic acid substrates in an amount 5 to 8 times that of templates are usually adequate. In conventional pyrosequencing, deposits such as degradation products of nucleic acid substrates are heaped up with the progress of the reaction and sometimes inhibit the reaction. In the present invention, a complementary strand synthesis reaction part and a luminescence reaction part are separated. Therefore, even a luminescence reaction chamber having a large size neither reduces the concentrations of substrates for complementary strand synthesis reaction nor influences complementary strand synthesis reaction. Furthermore, the influence of the deposits can be reduced by using a sufficient amount of a luminescence reaction solution. Thus, the luminescence reaction can be performed stably.

Figure 20:
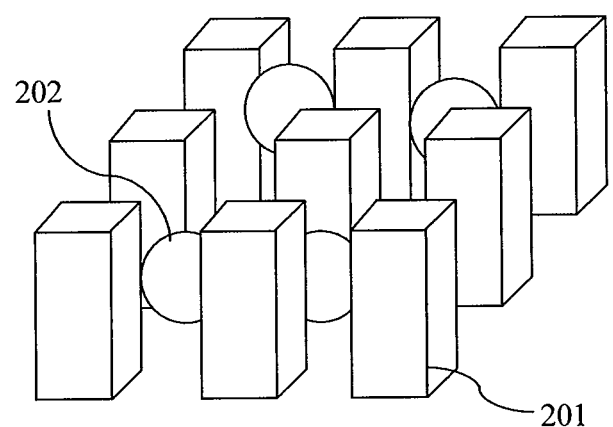
FIG. 20 is diagram showing a state in which beads have been captured by micropillars.

Here, the permanent magnet was used for holding the magnetic beads. Alternatively, a movable stage made of a magnetic material may be used for holding the magnetic beads, and the magnetic beads may be operated by attaching or removing a magnet to or from the magnetic material. Alternatively, DNA carrier beads may be used. In this case, as shown in FIG. 20, beads 202 are held by, for example, micropillars 201, and a plate comprising the micropillars attached thereto may be moved up and down. In this case, the beads that can be used as a DNA carrier are, in addition to magnetic beads, for example, Sepharose beads or ceramic beads. On the other hand, the micropillars are prepared by plastic molding and surface-treated. Then, these micropillars may be used as carriers designed to be capable of binding to DNA.

Example 5

In the present Example, DNAs are held by one to several tens of large beads. DNAs are bound to bead(s) of 0.5 mm in diameter through biotin-avidin bond to prepare template DNAs. The amount of DNAs immobilized on the surface is approximately $3 \times 10^{10}$ molecules per bead. When 10 beads are used, DNA templates corresponding to 0.5 pmol can be used. A photomultiplier used as a detector can give signals necessary for sequencing even from one bead. Alternatively, approximately 10 beads are preferably used for a simple photodiode used.

Figure 21:
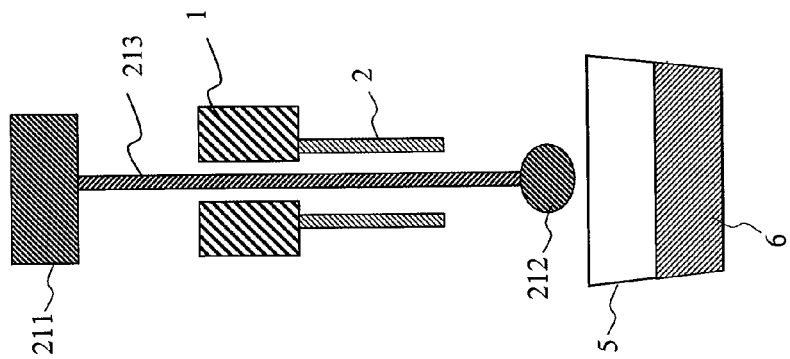
FIG. 21 is a diagram showing a state in which a magnet has been attached to a movable holding rod.
Figure 22:
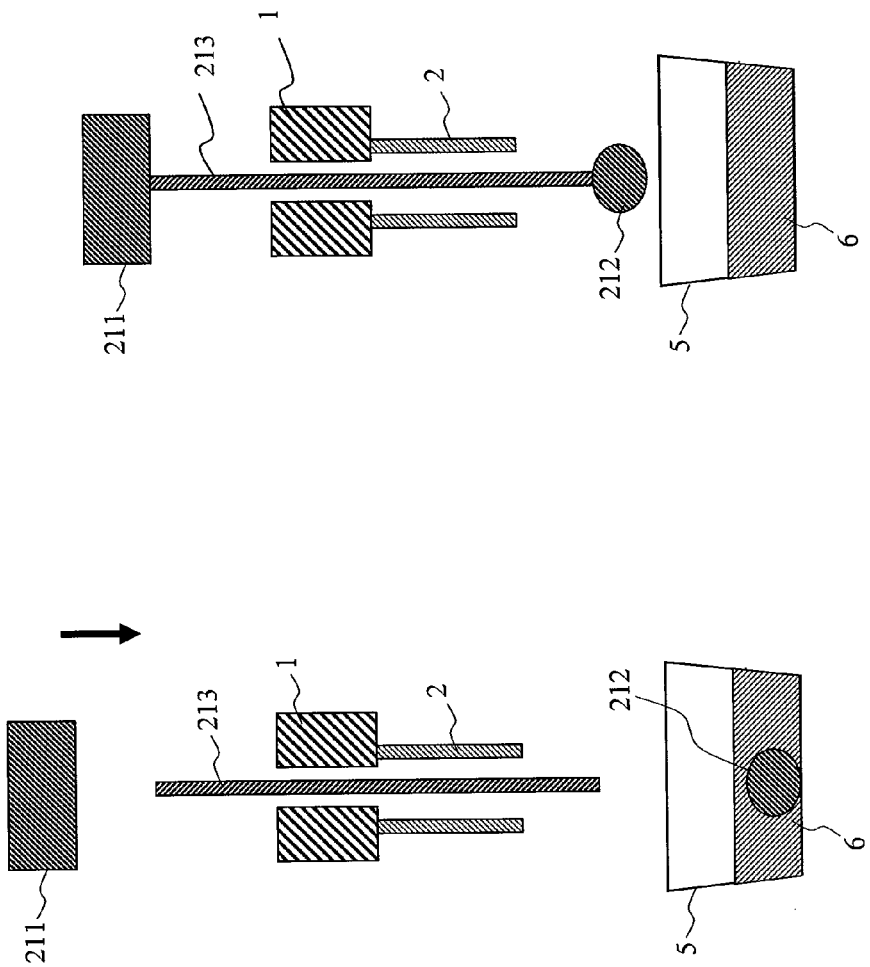
FIG. 22 is a diagram showing a state in which a magnet has been released from a holding rod.
Figure 23:
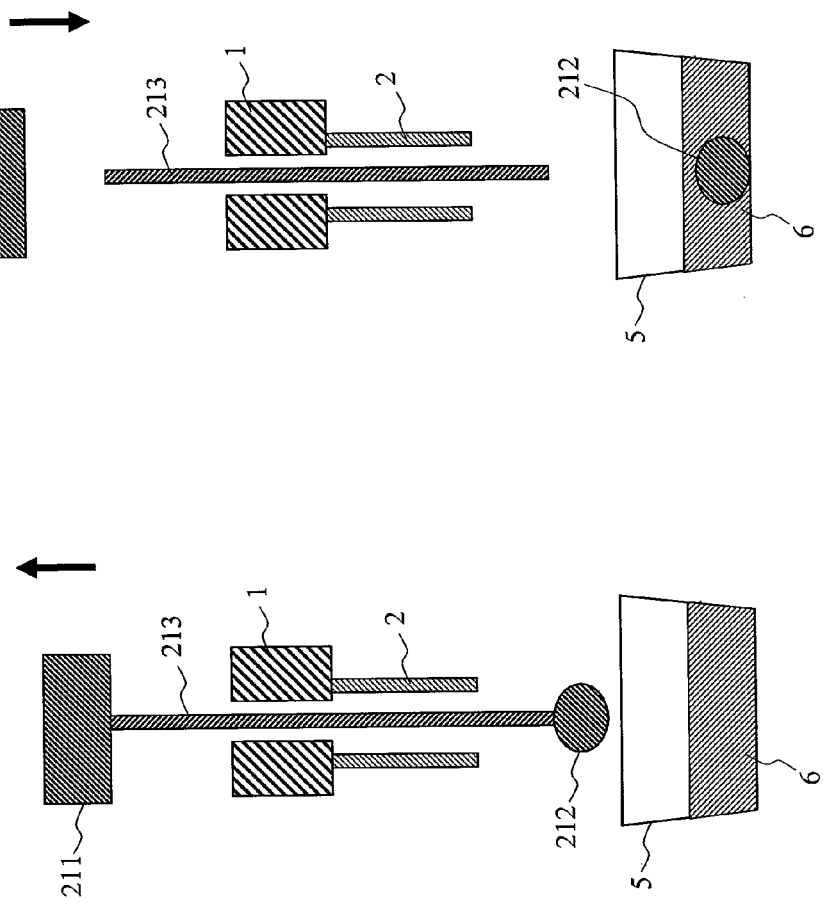
FIG. 23 is a diagram showing a state in which a magnet has been attached again to a holding rod.

FIGS. 21 to 23 are respectively a schematic diagram showing the structure of an apparatus of the present Example. For simplification, an example in which one bead is used is shown. A DNA-immobilized magnetic bead 212 is subjected to primer hybridization and DNA polymerase addition and then held, as shown in FIG. 21, by the tip of a holding rod 213 made of a magnetic material such as iron or permalloy. Four nucleic acid substrates are sequentially supplied onto the magnetic bead surface from capillaries 2 at the ends of dispensers 1. The holding rod 213 is in contact with a powerful magnet 211 and holds, at the tip thereof, the magnetic bead 212 through magnetic force. DNA complementary strand synthesis reaction proceeds when a nucleic acid substrate capable of being incorporated in the template DNA immobilized on the magnetic bead 212 is supplied. The DNA complementary strand synthesis reaction is completed in a few seconds. As a result, pyrophosphoric acid is produced. On the other hand, the added nucleic acid substrates are present around the magnetic bead 212 without being incorporated when they are non-complementary to the template and unused in complementary strand synthesis.

Next, as shown in FIG. 22, the magnet 211 is separated from the holding rod 213. The magnetic bead 212 falls under gravity and is sunk in a luminescence reaction solution 6. The pyrophosphoric acid and redundant nucleic acid substrates on the surface of the magnetic bead 212 are removed from the magnetic bead surface such that they are diffused into the luminescence reaction solution. The pyrophosphoric acid is converted to ATP, which in turn emits light through luciferase reaction. This light is detected by a photodetector. The redundant nucleic acid substrates are degraded by apyrase. Complementary strand synthesis reaction is performed separately from ATP-producing reaction and luminescence reaction and can therefore proceed fully.

Then, the magnet 211 is brought into contact with the holding rod 213. As shown in FIG. 23, the magnetic bead 212 is popped out of the solution 6 through magnetic force and adsorbed onto the tip of the holding rod 213. The holding rod 213 can be moved up and down. Therefore, the holding rod 213 can be dipped close to the magnetic bead 212 in the luminescence reaction solution 6 and taken out thereof after holding the magnetic bead at the tip thereof through magnetic force. Alternatively, when the powerful magnet 211 is used, the magnetic bead 212 can be taken out of the luminescence reaction solution 6 through magnetic force, with the holding rod 213 fixed on the magnet. Next nucleic acid substrates are supplied from the dispenser 1, and complementary strand synthesis reaction, ATP-producing reaction, and luminescence reaction are repeated.

Figure 24:
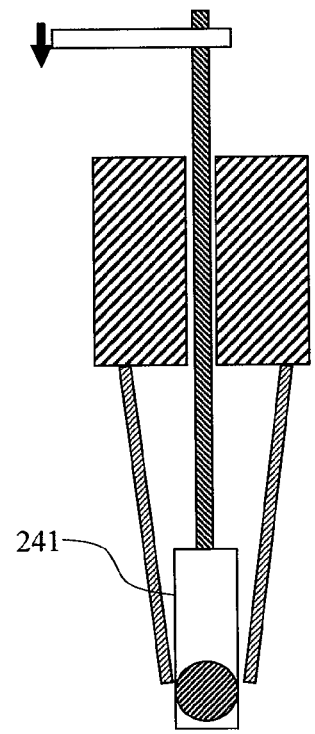
FIG. 24 is a sectional view of an apparatus in which beads have been captured by a holding part disposed at the end of a wire.

In the present Example, an example in which DNA and a by-product pyrophosphoric acid from complementary strand synthesis are transferred from the DNA complementary strand synthesis region to the ATP-producing/luminescence reaction region by use of magnetic force was disclosed. Of course, a bead, a wire 241, or rod may be attached to the bead for movement, as shown in FIG. 24. FIG. 24 is a sectional view of an apparatus in which the bead is captured by a holding part disposed at the tip of the wire. The use of such a holder eliminates the need of using magnetic force. The holding part together with the bead therein is dipped in a reaction solution after complementary strand synthesis reaction.

Here, the bead was held by the holding rod, and reagents were supplied from dispensers different from the holding rod. Alternatively, the nucleic acid substrates may be supplied from the tip of a holding rod in a pipe form. In this case, the holding rod serves as a dispenser pipe, and a washing solution is sent from the same pipe after every reagent supply to wash the reagent passage every time.

The magnetic bead in the present Example and the membrane in the preceding Examples are used as a supporter for DNA immobilization. However, in the present invention, the carrier used for holding DNA is not limited to these members. Any member may be used, such as porous materials, nylon filters, and other members capable of holding DNA through immobilization thereof or via DNA polymerase immobilized thereon.

Figure 25:
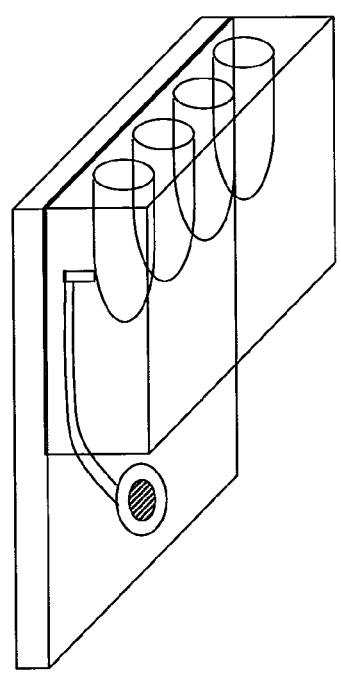
FIG. 25 is a diagram showing an example of an apparatus using a microfabrication device.

Alternatively, dNTPs may be supplied to the complementary strand synthesis reaction part by use of a microfabrication device as schematically shown in FIG. 25. FIG. 25 is a schematic diagram showing an example of an apparatus comprising a dispenser formed integrally with a holding part, which is made of a microfabrication device, instead of the nucleic acid substrate dispenser comprising a capillary.

The present invention can be used widely in, for example, DNA sequencing, DNA diagnostics, or DNA testing. Particularly, sequencing underlies the biological field. Thus, convenient and inexpensive sequencing methods have been demanded. In pyrosequencing, signals are optically detected by use of chemiluminescence. Unlike fluorescence detection, this approach does not require an excitation light source and therefore has the advantage that an apparatus with a simple structure can be achieved. Therefore, the pyrosequencing is a highly potential method that satisfies the requirements. However, in a conventional method of pyrosequencing, plural enzymatic reactions proceeded concurrently. Therefore, complementary strand synthesis reaction disadvantageously failed to fully proceed or proceeded too fast. The present invention can solve this problem. Thus, pyrosequencing can be expected to advance greatly. Moreover, complementary strand synthesis reaction can be performed in a state independent from other reactions using a small reaction volume, thus high concentrations of substances involved in the reaction and can therefore be done completely in a short time. Therefore, advantageously, the stepwise reaction can be short-cycled. As a result, the overall measurement time is shortened. Thus, according to the present invention, the application of pyrosequencing can be expected to be expanded to, for example, urgent genetic testing such as infectious disease testing that requires performing genetic testing in a short time.

What is claimed is:

1. A DNA analysis apparatus, comprising:
   a movable stage supporting a DNA holding carrier which holds a DNA sample;
   a substrate supplying part which individually supplies plural types of substrates for complementary strand synthesis to the DNA sample held by the DNA holding carrier;
   a reaction vessel which accommodates a reaction solution that produces luminescence through reaction with a DNA complementary strand synthesis reaction product, wherein the reaction solution contains Apyrase that degrades the substrates;
   a photodetector disposed proximal to the reaction vessel to detect luminescence produced in the reaction solution; and
   a computer to control positioning of the stage and control dispensing of the substrates for complementary strand synthesis onto the DNA holding carrier from the substrate supplying part, wherein
   the computer positions the stage so the DNA holding carrier is spatially separated from the reaction solution in the reaction vessel and the DNA holding carrier receives the substrates from the substrate supplying part for performing complementary strand synthesis, and then moves the stage so that the holding carrier is dipped into the reaction solution in the reaction vessel for performing a luminescence reaction and degrading the substrates by Apyrase.

2. The DNA analysis apparatus according to claim 1, wherein the reaction solution is contained in the reaction vessel in an amount exceeding an amount of the substrates for complementary strand synthesis supplied from the substrate supplying part.

3. The DNA analysis apparatus according to claim 1, wherein the DNA holding carrier is a membrane.

4. The DNA analysis apparatus according to claim 1, wherein the DNA holding carrier is a string-shaped member, beads, or magnetic beads.

5. The DNA analysis apparatus according to claim 1, wherein the DNA complementary strand synthesis reaction product is pyrophosphoric acid.

6. The DNA analysis apparatus according to claim 1, wherein the controlling part controls the position of the DNA holding carrier through the on/off control of magnetic force.

7. The DNA analysis apparatus according to claim 1, wherein the DNA sample is held by the DNA holding carrier either through direct immobilization or via an enzyme for complementary strand synthesis immobilized on the DNA holding carrier.

8. The DNA analysis apparatus according to claim 1, wherein the substrate supplying part supplies the substrates for complementary strand synthesis to the DNA sample from a reagent reservoir by use of a capillary or microfabrication device.

9. The DNA analysis apparatus according to claim 1, wherein the substrate supplying part and the reaction vessel are relatively fixed, and the DNA holding carrier is moved relatively to the substrate supplying part and the reaction vessel.

10. The DNA analysis apparatus according to claim 1, wherein the substrate supplying part and the DNA holding carrier are relatively fixed, and the substrate supplying part and the DNA holding carrier are moved relatively to the reaction vessel.

11. The DNA analysis apparatus according to claim 1, wherein the photodetector is located below the reaction vessel.

* * * * *

SEQUENCE LISTING

<160> NUMBER OF SEQ ID NOS: 3

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
aaaattactt accatttgcg atca                                          24

<210> SEQ ID NO 2
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
tttttttttt tttttttttt cattagttgc cattaatcca ggtgatcgca aatggtaagt    60
aattttt                                                             67

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
cctggattaa tggcaactaa tg                                            22